US006843791B2

(12) United States Patent
Serhan

(10) Patent No.: US 6,843,791 B2
(45) Date of Patent: Jan. 18, 2005

(54) LOCKING CAP ASSEMBLY FOR SPINAL FIXATION INSTRUMENTATION

(75) Inventor: Hassan A. Serhan, S. Easton, MA (US)

(73) Assignee: DePuy Acromed, Inc., Raynham, MA (US)

( * ) Notice: Subject to any disclaimer, the term of this patent is extended or adjusted under 35 U.S.C. 154(b) by 41 days.

(21) Appl. No.: 10/340,567

(22) Filed: Jan. 10, 2003

(65) Prior Publication Data

US 2004/0138660 A1 Jul. 15, 2004

(51) Int. Cl.[7] .............................................. A61B 17/70
(52) U.S. Cl. ...................................................... 606/61
(58) Field of Search ..................................... 606/61, 60

(56) References Cited

U.S. PATENT DOCUMENTS

| | | |
|---|---|---|
| 4,611,580 A | 9/1986 | Wu |
| 4,743,260 A | 5/1988 | Burton |
| 4,763,644 A | 8/1988 | Webb |
| 4,790,297 A | 12/1988 | Luque |
| 4,805,602 A | 2/1989 | Puno et al. |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines, Jr. |
| 5,005,562 A | 4/1991 | Cotrel |
| 5,129,388 A | 7/1992 | Vignaud et al. |
| 5,154,719 A | 10/1992 | Cotrel |
| 5,217,497 A | 6/1993 | Mehdian |
| 5,261,912 A | 11/1993 | Frigg |
| 5,261,913 A | 11/1993 | Marnay |
| 5,360,431 A | 11/1994 | Puno et al. |
| 5,385,583 A | 1/1995 | Cotrel |
| 5,403,315 A * | 4/1995 | Ashman ....................... 606/61 |
| 5,437,669 A | 8/1995 | Yuan et al. |
| 5,474,555 A | 12/1995 | Puno et al. |
| 5,476,464 A | 12/1995 | Metz-Stavenhagen et al. |
| 5,520,689 A | 5/1996 | Schlapfer et al. |
| 5,527,314 A * | 6/1996 | Brumfield et al. ............ 606/61 |
| 5,536,268 A | 7/1996 | Griss |
| 5,554,157 A | 9/1996 | Errico et al. |
| 5,669,911 A | 9/1997 | Errico et al. |
| 5,683,390 A | 11/1997 | Metz-Stavenhagen et al. |
| 5,690,630 A | 11/1997 | Errico et al. |
| 5,697,929 A | 12/1997 | Mellinger |

(List continued on next page.)

FOREIGN PATENT DOCUMENTS

| | | | |
|---|---|---|---|
| DE | 3722590 C1 | 7/1987 | |
| FR | 87 17852 | 12/1987 | |
| GB | 2 173 104 A | 10/1986 | |
| WO | WO 00/25689 | * 5/2000 | ........... A61B/17/70 |

Primary Examiner—Kevin Shaver
Assistant Examiner—Michael B. Priddy
(74) Attorney, Agent, or Firm—Nutter McClennen & Fish LLP

(57) ABSTRACT

A locking cap assembly for locking a spinal fixation element to a spinal fixation element receiving body includes an outer and inner locking element. The outer locking element has a proximal mating element, and a engagement element formed on the inner surface adjacent the distal end for engaging a spinal fixation element receiving body so as to close the spinal fixation element to the spinal fixation element receiving body upon tightening. The inner locking element has a deformable spinal fixation element contacting ring disposed on its distal end and a proximal mating element on its proximal end rotatably mated to the outer locking element proximal mating element so that the inner locking element is rotatably mounted within the outer locking element. Tightening the spinal fixation locking cap assembly to the spinal fixation element receiving body causes the deformable spinal fixation element contacting ring to contact the spinal fixation element and to deform the deformable spinal fixation element contacting ring to provide secure four point locking of the spinal fixation element within the spinal fixation element receiving body.

40 Claims, 3 Drawing Sheets

U.S. PATENT DOCUMENTS

| | | |
|---|---|---|
| 5,713,898 A | 2/1998 | Stucker et al. |
| 5,716,356 A | 2/1998 | Biedermann et al. |
| 5,733,286 A | 3/1998 | Errico et al. |
| 5,738,685 A | 4/1998 | Halm et al. |
| 5,752,957 A | 5/1998 | Ralph et al. |
| 5,797,911 A | 8/1998 | Sherman et al. |
| 5,863,293 A | 1/1999 | Richelsoph |
| 5,879,350 A | 3/1999 | Sherman et al. |
| 5,882,350 A | 3/1999 | Ralph et al. |
| 5,910,142 A | 6/1999 | Tatar |
| 5,964,760 A | 10/1999 | Richelsoph |
| 5,989,254 A | 11/1999 | Katz |
| 6,443,953 B1 | 9/2002 | Perra et al. |
| 6,471,705 B1 * | 10/2002 | Biedermann et al. ......... 606/61 |
| 6,520,963 B1 * | 2/2003 | McKinley ................... 606/61 |
| 2004/0039383 A1 * | 2/2004 | Jackson ..................... 606/61 |

* cited by examiner

LOCKING CAP ASSEMBLY FOR SPINAL FIXATION INSTRUMENTATION

FIELD OF THE INVENTION

The present invention relates to devices and systems for holding a spinal fixation element. More particularly, the invention provides closure systems including at least an outer locking cap and having an inner locking element having a deformable ring configured for attaching a spinal fixation element to a vertebral coupling system such as a pedicle screw or a hook.

BACKGROUND OF THE INVENTION

The use of spinal fixation instrumentation to align and/or fix a desired relationship between adjacent vertebral bodies is well established. Such instrumentation typically includes a spinal fixation element, such as a relatively rigid fixation rod, that is coupled to adjacent vertebrae by attaching the element to pedicle screws which have been inserted into the patient's vertebrae or to spinal hooks which can be placed into a vertebral arch for coupling to the vertebral bodies. Once installed, the spinal fixation instrumentation holds the vertebrae in a desired spatial relationship, either until desired healing or spinal fusion has taken place, or for some longer period of time.

One example of a rod based spinal fixation system is provided in U.S. Pat. No. 5,005,562, issued Apr. 9, 1991 to Cotrel (which is hereby incorporated by reference). This system includes pedicle screws and spinal hook vertebral coupling elements (both screws and hooks) having integral U-shaped bodies that extend outward from the vertebrae to which they are attached. A spinal fixation rod is shaped as desired and fitted into the "U" of U-shaped bodies of adjacent vertebrae. The inner surfaces of the U-shaped body are threaded to accept a set screw, and rod is fixed to the vertebral coupling elements by threading a set screw into each of the U-shaped bodies to lock in the rod.

U.S. Pat. No. 5,545,165, issued Aug. 13, 1996 to Biedermann et al. (and incorporated herein by reference), illustrates an improvement in closure systems for fixing a rod to vertebral coupling elements over those provided by Cotrel. The Biedermann et al. system also uses pedicle screws and spinal hooks having U-shaped bodies that extend outward from the vertebrae to which they are attached. The U-shaped bodies of the Biedermann et al. system are threaded on both the inside and the outside. The rod is therefore locked in by both an inner set screw and an outer lock nut. In the illustrated embodiments, the inner set screw is adapted to be driven on its threads using a hex-shaped driver element, and the outer locking nut is provided with hex-shaped flat outer surfaces suitable for engagement with a wrench or similar driving tool.

U.S. Pat. No. 5,443,467, issued Aug. 22, 1995 to Biedermann et al. (and incorporated herein by reference) illustrates the use of an inner set screw and an outer lock nut to lock a rod into a U-shaped body in a polyaxial screw system. The use of these two elements to lock a rod can result in a "four point contact" between the two locking elements and the rod—that is, each of the inner set screw and outer lock nut can contact the rod in two places, resulting in four contact points that lock the rod down. In this system, a pedicle screw having a spherical head is captured within a separate U-shaped receiver body. The angle of the screw with respect to the body can be changed until a head-locking element is tightened to lock the angle of the screw head within the receiver body. According to Biedermann et al., this combination of an inner set screw and an outer locking nut provides an advantage in that the force acting on the rod can be independently adjusted by either the inner set screw or the outer locking nut—a particularly useful advantage where the rod being fastened is curved and an exact fastening might only be possible by independent adjustment of the two closure elements. In addition, when tightened, the inner set screw and the outer locking nut tend to lock each other in their tightened positions.

While the closure systems of the Biedermann et al. patents have been quite successful, the illustrated embodiments necessarily involve the tightening of two separate elements using two separate tools. It would be beneficial to provide a single locking nut assembly that could lock a rod down with a four point contact, but require only a single tool and a single locking step by the surgeon.

SUMMARY OF THE INVENTION

The present invention provides a locking assembly for holding a spinal fixation element. In a first aspect, the invention includes a locking cap assembly for locking a spinal fixation element to a spinal fixation element receiving body. The assembly includes inner and outer locking elements. The outer locking element has a proximal and distal end and inner and outer surfaces. The outer locking element has a proximal mating element, and an engagement element which is formed on the inner surface adjacent the distal end for engaging a spinal fixation element receiving body so as to close the spinal fixation element to the spinal fixation element receiving body upon tightening of the engagement element.

The inner locking element also has a proximal and a distal end. A deformable spinal fixation element contact ring sits on the distal end while a proximal mating element can be found at the proximal end. The proximal mating element is rotatably mated to the outer locking element's proximal mating element so that the inner locking element is rotatably mounted within the outer locking element.

When the spinal fixation locking cap assembly is tightened to the spinal fixation element receiving body to lock the spinal fixation element therein, it causes the deformable spinal fixation element contacting ring to contact the spinal fixation element and to deform the deformable spinal fixation element contacting ring to provide secure four point locking of the spinal fixation element within the spinal fixation element receiving body.

In a further aspect of the invention, a system for coupling a spinal fixation element to a patient's spine is provided having a spinal fixation element receiving body with a vertebral coupling disposed on a first end of the body and a spinal fixation element receiving opening formed on a second end of the body. The body includes an outer portion adapted to engage an outer locking element. A spinal fixation element may be received with the spinal fixation element receiving body.

A locking cap assembly locks the spinal fixation element to the spinal fixation element receiving body, and includes an outer and an inner locking element. The outer locking element has opposed proximal and distal ends and inner and outer surfaces. The outer locking element has a proximal mating element, and an engagement element which is formed on the inner surface adjacent the distal end for engaging the outer portion of the spinal fixation element receiving body so as to close the spinal fixation element to the spinal fixation element receiving body upon tightening of the engagement element.

The inner locking element also has a proximal and a distal end. A deformable spinal fixation element contact ring sits on the distal end while a proximal mating element can be found at the proximal end. The proximal mating element is rotatably mated to the outer locking element's proximal mating element so that the inner locking element is rotatably mounted within the outer locking element.

When the spinal fixation locking cap assembly is tightened to the spinal fixation element receiving body to lock the spinal fixation element therein, it causes the deformable spinal fixation element contacting ring to contact the spinal fixation element and to deform the deformable spinal fixation element contacting ring to provide secure four point locking of the spinal fixation element within the spinal fixation element receiving body.

A still further aspect of the invention provides a locking cap assembly for locking a spinal fixation element to a spinal fixation element receiving body including an inner and an outer locking element.

The outer locking element has opposed proximal and distal ends and inner and outer surfaces, including an proximal mating element. The inner locking element has proximal and distal ends with a proximal mating element on its proximal end rotatably mated to the outer locking element proximal mating element so that the inner locking element is rotatably mounted within the outer locking element.

One of the inner and outer locking elements has an engagement element for engaging a spinal fixation element receiving body so as to close the spinal fixation element to the spinal fixation element receiving body upon tightening of the engagement element. The other locking element has a deformable spinal fixation element contacting ring disposed on its distal end.

When the spinal fixation locking cap assembly is tightened to the spinal fixation element receiving body to lock the spinal fixation element therein, it causes the deformable spinal fixation element contacting ring to contact the spinal fixation element and to deform the deformable spinal fixation element contacting ring to provide secure locking of the spinal fixation element within the spinal fixation element receiving body.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides locking cap assemblies and systems that provide the benefits of known spinal fixation closure systems, including a secure four point contact closure of a spinal fixation element (even where that element is a curved rod), but also being lockable in a single locking step with a single locking tool by a surgeon. A locking cap assembly 10 of the invention that may be used to fix a spinal fixation element 11 (such as a spinal fixation rod) to a vertebral coupling element (such as polyaxial and monoaxial pedicle screws and spinal hooks) is illustrated in FIGS. 1 (showing the locking cap alone) and 2 (showing the locking cap in contact with a spinal fixation rod).

Figure 1:
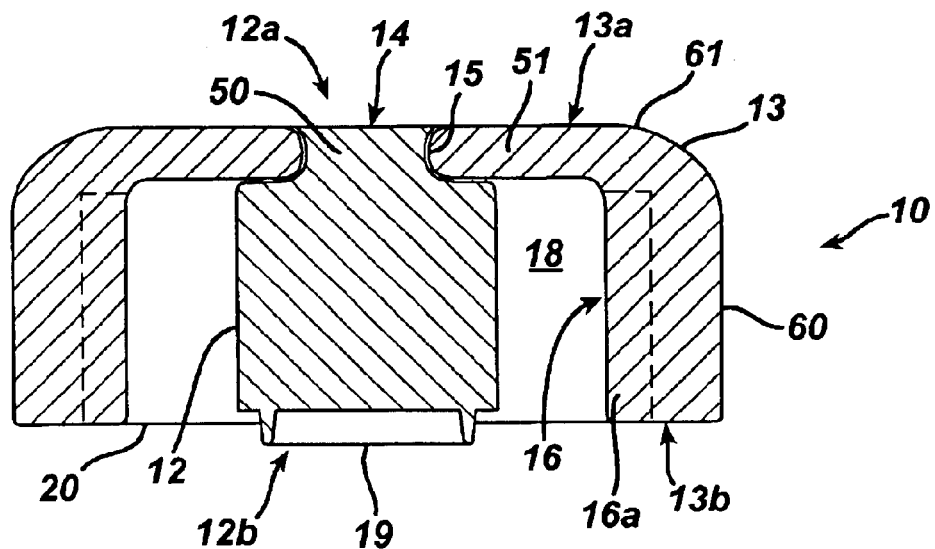
FIG. 1 is a cross-sectional view of a locking cap assembly of the invention.
Figure 2:
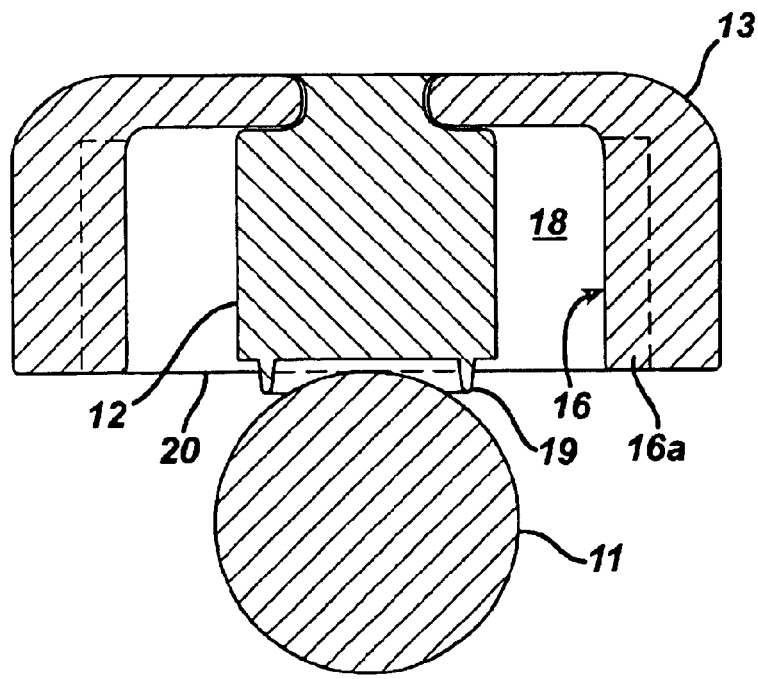
FIG. 2 is a cross-sectional view of a locking cap assembly of the invention shown contacting of the invention shown contacting spinal fixation rod.

FIGS. 1 and 2 show an inner locking element 12 and an outer locking element 13 of the locking cap assembly 10. The inner locking element has a proximal end 12a and a distal end 12b. The outer locking element has a proximal end 13a and a distal end 13b. The inner and outer locking elements 12, 13 are rotatably connected at their proximal ends 12a, 13a. The rotatable connection 14 allows the inner and outer locking elements 12, 13 to spin in either direction with respect to each other. In the embodiment illustrated in FIGS. 1 and 2 the rotatable connection is provided by an annular groove 15 formed on a spindle 50 on the proximal end of 12a of the inner locking element 12 into which a cap portion 51 of the outer locking element 13 is seated and thereby rotatably attached. In this embodiment, the rotatable connection 14 between the inner locking element 12 and outer locking element 13 will not allow the inner and outer locking elements 12, 13 to move relative to one another except for rotation. The inner and outer locking elements 12, 13 may also be rotatably connected in other ways known to one of ordinary skill in the art. Examples of other rotatable connections could include a slotted arrangement, a spindle arrangement, a threaded arrangement or a ball bearing arrangement.

In one embodiment, the longitudinal motion between the inner 12 and the outer 13 locking elements may be provided. For example, the outer locking element 13, particularly cap portion 51, can be constructed of resilient material that allows some additional longitudinal movement between the locking elements 12, 13. Additional movement may be of particular importance where the spinal fixation element 11 is bent or curved. When a spinal fixation element 11 is straight, all four contact points (two on each of the inner and outer locking elements) can sit evenly on the spinal fixation element 11. When the spinal fixation element is curved or bent the additional freedom of movement between the inner and outer locking elements 12, 13 allows the contact points on the inner and outer locking elements to individually conform to the spinal fixation element. The longitudinal motion between the locking elements 12, 13 can thus allow further four point contact with a bent or curved spinal fixation element 11.

Figure 3:
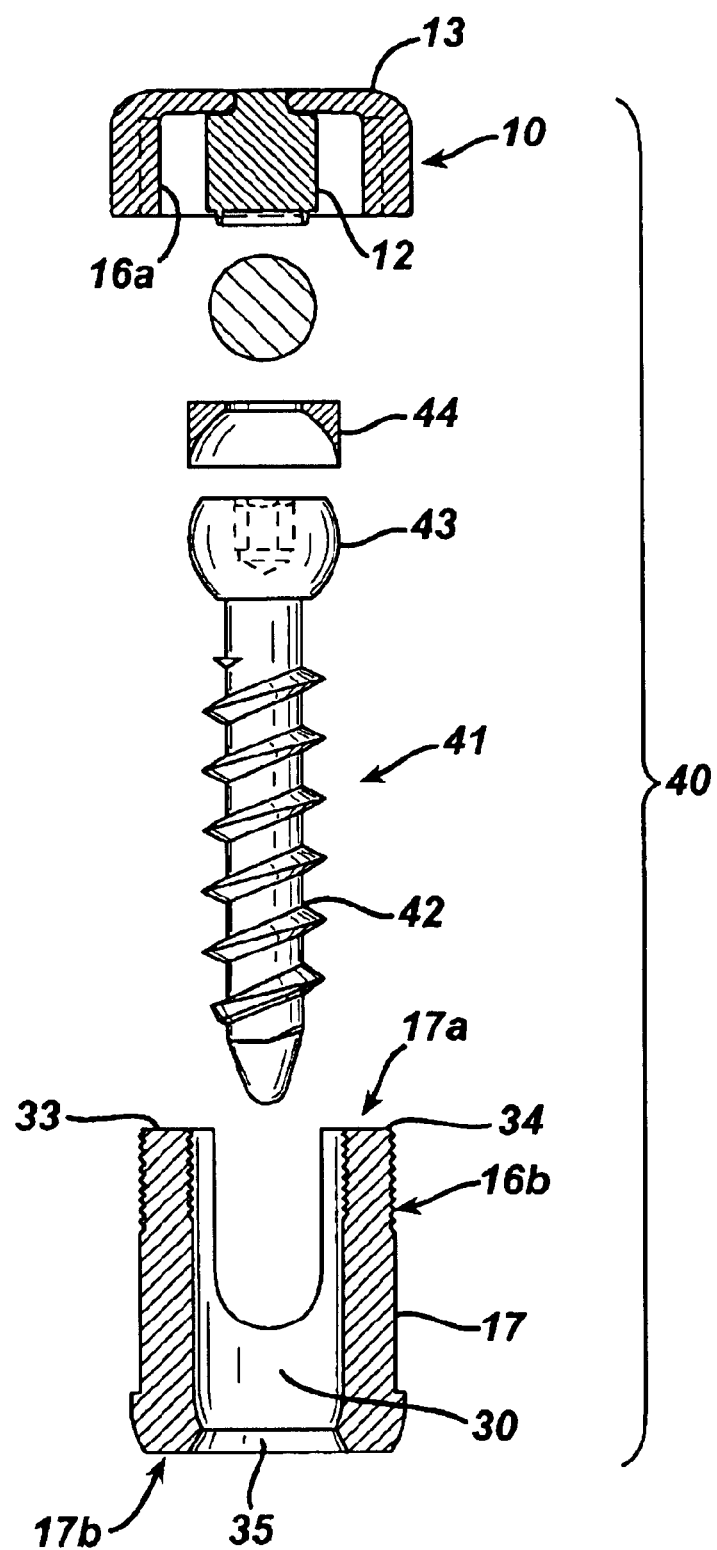
FIG. 3 is an exploded view of the locking cap assembly of FIG. 1 in use with a polyaxial pedicle screw vertebral coupling system.

The inner surface of the outer locking element 13 has inner engagement element 16 for engaging a vertebral coupling receiving body 17 (receiving body 17 is illustrated in FIG. 3). The inner engaging element 16 may include threads 16a on the inner surface of the outer locking element which engages opposing threads 16b on the outside of the receiving body 17. Rotating the outer locking element 13 thus engages the threads 16a on the outer locking element 13 with the opposing threads 16b on the receiving body 17 to tighten the locking cap assembly 10. While threads are illustrated as an inner engagement element 16 for the outer locking element 13, a person of ordinary skill in the art will recognize that other suitable engaging elements, such as for example a tightenable pin and groove configuration, or a twist-lock flange arrangement such as that illustrated in U.S. patent application Ser. No. 09/667,937, filed Sep. 22, 2000, to Bono et al., and commonly assigned (which is hereby incorporated by reference) could serve to engage the outer locking element to a spinal fixation element receiving body so as to tighten and hold a spinal fixation element therein.

The outer locking element 13 can also have an outer surface 60 onto which a tool can be fitted to tighten the locking cap assembly 10. The outer surface of the outer locking assembly 13 may have flat areas which a tool can grip for tightening. Any surface that allows a tool to grip could be used, for example, a surface with holes or slots which receives prongs from a tool for tightening. In addition, tool engagement surfaces could be provided on proximal cap portion 61 to minimize the lateral area needed to install the locking cap 10.

In the illustrated embodiment, the inner locking element 12 and the outer locking element 13 each have a cylindrical shape with space 18 between the inner and outer locking elements 12, 13 to receive upper walls of a receiving body 17. When the locking cap assembly 10 is assembled with the receiving body 17, preferably only minimal space exists between the inner locking element 12, the receiving body 17 and the outer locking element 13. In this way, the inner locking element will retard any inward deflection of the upper walls of the receiving body as a result of tightening the threaded engagement.

The distal end of the inner locking element 12 has a deformable spinal fixation element contacting element 19. The deformable element 19 comes in contact with the spinal fixation element 11 and creates two of the four points of contact between the locking cap assembly 10 and the spinal fixation element 11. As the locking cap assembly 10 is tightened to the spinal fixation element 11, the deformable element 19 contacts the spinal fixation element 11 before the distal end of the outer locking element 13 first contacts the spinal fixation element 11. The pressure from the tightening of the locking cap assembly 10 then causes the deformable element 19 to deform to the shape of the spinal fixation element 11 as shown in FIG. 2.

This embodiment of the invention can also be configured so that no notching or scoring of the spinal fixation element 11 occurs upon tightening of the locking cap assembly 10. In some prior art devices, locking caps notch spinal fixation rods upon tightening of the locking cap for increased securement of the rod and to indicate that tightened cap has been properly loaded. Such notching or scoring of the rod, however, especially when the rod is formed of materials such as titanium or titanium alloys, can cause reduced fatigue performance in the rod. In the present configuration, however, because the inner and outer locking elements 12, 13 are rotatably connected, and because deformable element 19 is deformable, the inner locking element 12 stops rotating with the outer locking element 13 once pressure is applied between the deformable element 19 and the spinal fixation element 11—thus ending relative motion between the deformable element 19 and the spinal fixation element 11 and beginning deformation of the deformable element without notching or scoring the spinal fixation element as occurs in the prior art.

The deformable element 19 is preferably in the shape of an annular ring that protrudes from the distal end of the locking cap assembly 10 further than the distal end of the outer locking cap assembly 13. After the locking cap assembly 10 has been tightened the locking cap assembly 10 and spinal fixation element 11 have the cross section shown in FIG. 2. In FIG. 2 the ring 19 of deformable material at the distal end 12b of the inner locking element 12 is partly deformed and in contact with the spinal fixation element 11 in two places. In the illustrated embodiment, the ring 19 is not so deformed that the spinal fixation device 11 can contact the center of the distal end of the inner locking element 12 and the spinal fixation element 11 and the inner locking element 12 only contact each other along the ring 19. Preferably, the spinal fixation element 11 and the inner locking element 12 form two contact points at opposite sides of the ring 19. Line 20 (partly ghosted) shows the plane in which the distal edge of outer locking element 13 contacts the spinal fixation element 11 to provide four point contact.

As the surgeon tightens the locking cap assembly 10, and the ring 19 of deformable material contacts the spinal fixation element 11, he or she will receive some feedback. It will become more difficult for the surgeon to continue tightening the locking cap assembly 10. The feedback will allow a surgeon to determine when the locking cap assembly 10 is tight enough and the four points have been properly engaged.

In one embodiment, the deformable element 19 become cold welded to the spinal fixation element 11 upon tightening of cap 10. The pressure from tightening the locking cap assembly 10 causes a cold welded bond between the spinal fixation element and the locking cap assembly. As a person of ordinary skill in the art will recognize, cold welding, which results from the pressure on the deformable ring 19 during tightening (see for examples of cold welding, U.S. Pat. Nos. 4,605,156 and 4,756,465, included herein by reference), adds strength to the fixation of spinal fixation element 11 by locking cap assembly 10.

The components in the locking cap assembly 10 can be made up uniform material or the components may be composed of different materials. Preferable materials include titanium, titanium alloys, stainless steels and other strong, biocompatible materials know to those skilled in the art.

As most clearly shown in FIG. 1, the deformable ring 19 decreases in thickness from its proximal to its distal end. In this way, the amount of feedback to the surgeon, as well as the amount of pressure needed to deform the ring, increases with increased tightening of locking cap assembly 10. While the precise dimensions of deformable ring 19 will depend on the materials used and the desired deformation characteristics, in a typical spinal rod fixation system and using titanium alloys, the deformable ring can preferably have a height of about 1 to 6 millimeters and more preferably between about 1.5 to 3 millimeters, and a maximum cross-sectional thickness of about 0.5 to 2 millimeters and more preferably between about 0.5 to 1 millimeters. In the illustrated embodiment, the height to maximum thickness ratio is approximately 3 to 1, and the thickness decreases continuously along the height of the ring. In addition, the illustrated ring is configured to deform over more than one half of its height.

Figure 4:
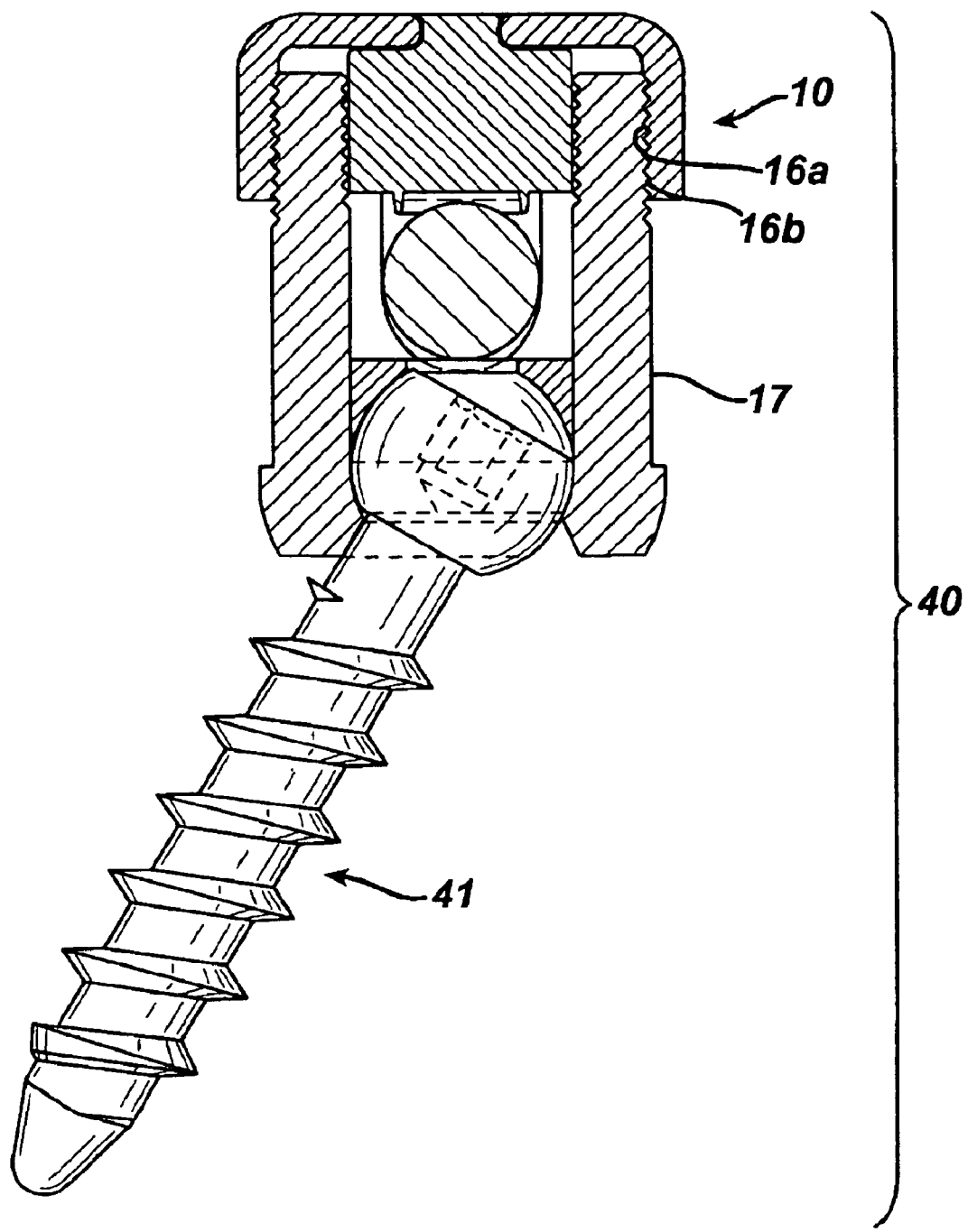
FIG. 4 is a side view with partial cross sectioning of the locking cap assembly of FIG. 1 in use with a polyaxial pedicle screw vertebral coupling system.

Locking cap assembly 10 is illustrated in FIG. 3 in an exploded cross-sectional view of a vertebral coupling system 13, and in an assembled vertebral coupling system in FIG. 4. Vertebral coupling system 13 includes a generally cylindrical receiver body 17 defining a central bore 30. The proximal end 17a of the receiver defines a rod receiving "U" shape 32 that defines the proximal end of the receiver into two legs 33, 34. Receiver body 17 also includes threads 16b at its proximal end 17a. At the distal end 17b of receiver 17, inner bore 30 includes a spherical region 35 configured to articulate with a spherical screw head.

Vertebral coupling system 40 also includes pedicle screw 41 having a distal threaded shaft 42 for attachment to a vertebral body and a spherical head 43. Spherical head 43 is configured to articulate with spherical region 35 on assembly of the vertebral coupling system 40.

Head fixing element 44 (FIG. 3) is provided within central bore 30 of receiver body 17 to press spherical head 43 into locking contact with spherical region 35 upon tightening of the entire vertebral coupling system 40. Spinal fixation rod 11 fits within U-shaped opening 32 of receiver body 17 and presses on head fixing element 44 to lock the angle of pedicle screw 41 with respect to the receiver. Locking cap assembly is engaged to outer threads 16b of receiver body 17 to independently lock rod 11 into U-shaped opening 32.

A person of ordinary skill in the art will recognize that, while the embodiment described above may be preferred, other embodiments of the locking cap of the invention are possible using the deformable ring described above to provide secure locking for a spinal fixation element. For example, in one embodiment, the inner locking element could be provided with the engaging element for tightening down the locking cap assembly. This engaging element could be threads provided on the outside of the inner locking element cylinder, or one of the other locking elements described above. The outer locking element can then be provided with the deformable ring on its distal end. In this way, a tool engaging feature can be provided on the proximal end of the inner locking element (such as an internal hex drive or some other drive feature known in the art) so that as the inner locking element is tightened to the spinal fixation element receiving body to lock the spinal fixation element therein, the deformable spinal fixation element contacting ring contacts the spinal fixation and deforms the deformable spinal fixation element contacting ring to provide secure locking of the spinal fixation element within the spinal fixation element receiving body. The benefits of the invention can thus be employed by providing the engagement element on either of the inner or outer locking element with the engagement element for tightening the locking cap down provided on the other.

A person of ordinary skill in the art will appreciate further features and advantages of the invention based on the above-described embodiments. For example, the closure devices and systems of the invention can be used with a variety of vertebral coupling elements in addition to the polyaxial pedicle screw illustrated in FIGS. 4 and 5 above. By way of specific examples, the closure devices and systems of the invention could be used with vertebral coupling elements such as mono-axial pedicle screws (see, e.g., FIGS. 1 to 4 of U.S. Pat. No. 5,725,527 to Biedermann et al. which is incorporated herein by reference) or spinal hooks (see, e.g., FIG. 5 of Biedermann et al.). Accordingly, the invention is not to be limited by what has been particularly shown and described, except as indicated by the appended claims. All publications and references cited herein are expressly incorporated herein by reference in their entity.

What is claimed is:

1. A locking cap assembly for locking a spinal fixation element to a spinal fixation element receiving body, comprising:
   an outer locking element having opposed proximal and distal ends and inner and outer surfaces, the outer locking element having a proximal mating element; and
   an inner locking element having proximal and distal ends, the inner locking element having a proximal mating element on its proximal end rotatably mated to the outer locking element proximal mating element so that the inner locking element is rotatably mounted within the outer locking element;
   a first one of the inner and outer locking elements having an engagement element formed thereon for engaging a spinal fixation element receiving body so as to close the spinal fixation element to the spinal fixation element receiving body upon tightening of the engagement element; and
   a second one of the inner and outer locking elements having a deformable spinal fixation element contacting ring disposed on its distal end;
   wherein tightening the spinal fixation locking cap assembly to the spinal fixation element receiving body to lock the spinal fixation element therein causes the deformable spinal fixation element contacting ring to contact the spinal fixation element and to deform the deformable spinal fixation element contacting ring to provide secure locking of the spinal fixation element within the spinal fixation element receiving body.

2. A locking cap assembly for locking a spinal fixation element to a spinal fixation element receiving body, comprising:
   an outer locking element having opposed proximal and distal ends and inner and outer surfaces, the outer locking element having a proximal mating element and an engagement element formed on the inner surface adjacent the distal end for engaging a spinal fixation element receiving body so as to close the spinal fixation element to the spinal fixation element receiving body upon tightening of the engagement element; and
   an inner locking element having proximal and distal ends, the inner locking element having a deformable spinal fixation element contacting element disposed on its distal end and a proximal mating element on its proximal end rotatably mated to the outer locking element proximal mating element so that the inner locking element is rotatably mounted within the outer locking element;
   wherein tightening the spinal fixation locking cap assembly to the spinal fixation element receiving body to lock the spinal fixation element therein causes the deformable spinal fixation element contacting element to contact the spinal fixation element and to deform the deformable spinal fixation element contacting element to provide secure locking of the spinal fixation element within the spinal fixation element receiving body; and
   wherein the deformable spinal fixation element contacting element is configured, upon deformation, to form a cold weld with a spinal fixation element.

3. A locking cap assembly for locking a spinal fixation element to a spinal fixation element receiving body, comprising:
   an outer locking element having opposed proximal and distal ends and inner and outer surfaces, the outer locking element having a proximal mating element and an engagement element formed on the inner surface adjacent the distal end for engaging a spinal fixation element receiving body so as to close the spinal fixation element to the spinal fixation element receiving body upon tightening of the engagement element; and
   an inner locking element having proximal and distal ends, the inner locking element having a deformable spinal fixation element contacting element disposed on its distal end and a proximal mating element on its proximal end rotatably mated to the outer locking element proximal mating element so that the inner locking element is rotatably mounted within the outer locking element;

wherein tightening the spinal fixation locking cap assembly to the spinal fixation element receiving body to lock the spinal fixation element therein causes the deformable spinal fixation element contacting element to contact the spinal fixation element and to deform the deformable spinal fixation element contacting element to provide secure locking of the spinal fixation element within the spinal fixation element receiving body; and wherein the deformable spinal fixation element contacting element is in the form of a ring configured to provide secure four point locking of the spinal fixation element by the locking cap assembly.

4. A locking cap assembly for locking a spinal fixation element to a spinal fixation element receiving body, comprising:

an outer locking element having opposed proximal and distal ends and inner and outer surfaces, the outer locking element having a proximal mating element and an engagement element formed on the inner surface adjacent the distal end for engaging a spinal fixation element receiving body so as to close the spinal fixation element to the spinal fixation element receiving body upon tightening of the engagement element; and an inner locking element having proximal and distal ends, the inner locking element having a deformable spinal fixation element contacting element disposed on its distal end and a proximal mating element on its proximal end rotatably mated to the outer locking element proximal mating element so that the inner locking element is rotatably mounted within the outer locking element;

wherein tightening the spinal fixation locking cap assembly to the spinal fixation element receiving body to lock the spinal fixation element therein causes the deformable spinal fixation element contacting element to contact the spinal fixation element and to deform the deformable spinal fixation element contacting element to provide secure locking of the spinal fixation element within the spinal fixation element receiving body; and wherein the inner locking element contacts the spinal fixation element at two points and the outer locking element contact the spinal fixation element at two points.

5. An assembly for locking a spinal fixation element to a spinal fixation element receiving body, comprising:

a spinal fixation element; and a spinal fixation locking cap assembly, comprising:

an outer locking element having opposed proximal and distal ends and inner and outer surfaces, the outer locking element having a proximal mating element and an engagement element formed on the inner surface adjacent the distal end for engaging a spinal fixation element receiving body so as to close the spinal fixation element to the spinal fixation element receiving body upon tightening of the engagement element; and an inner locking element having proximal and distal ends, the inner locking element having a deformable spinal fixation element contacting element disposed on its distal end and a proximal mating element on its proximal end rotatably mated to the outer locking element proximal mating element so that the inner locking element is rotatably mounted within the outer locking element;

wherein tightening the spinal fixation locking cap assembly to the spinal fixation element receiving body to lock the spinal fixation element therein causes the deformable spinal fixation element contacting element to contact the spinal fixation element and to deform the deformable spinal fixation element contacting element to provide secure locking of the spinal fixation element within the spinal fixation element receiving body; and wherein the spinal fixation element is curved and the inner locking element contacts the spinal fixation element at two points and the outer locking element contact the spinal fixation element at two points.

6. A locking cap assembly for locking a spinal fixation element to a spinal fixation element receiving body, comprising:

an outer locking element having opposed proximal and distal ends and inner and outer surfaces, the outer locking element having a proximal mating element and an engagement element formed on the inner surface adjacent the distal end for engaging a spinal fixation element receiving body so as to close the spinal fixation element to the spinal fixation element receiving body upon tightening of the engagement element; and an inner locking element having proximal and distal ends, the inner locking element having a deformable spinal fixation element contacting element disposed on its distal end and a proximal mating element on its proximal end rotatably mated to the outer locking element proximal mating element so that the inner locking element is rotatably mounted within the outer locking element;

wherein the deformable spinal fixation element contacting element extends from a first position at the distal end of the inner locking element that is proximal to the distal end of the outer locking element to a second position distal to the distal end of the outer locking element; and wherein tightening the spinal fixation locking cap assembly to the spinal fixation element receiving body to lock the spinal fixation element therein causes the deformable spinal fixation element contacting element to contact the spinal fixation element and to deform the deformable spinal fixation element contacting element to provide secure locking of the spinal fixation element within the spinal fixation element receiving body.

7. The assembly of claim 6, wherein the engagement element comprises threads formed on the inner surface adjacent to the distal end.

8. The assembly of claim 7, wherein upon deformation of the deformable spinal fixation element contacting element upon tightening of the outer locking element to a spinal fixation receiving element by turning, the inner locking element does not rotate with the turn of the outer locking element.

9. The assembly of claim 6, wherein a driving element is formed on the outer surface of the outer locking element.

10. The assembly of claim 9, wherein the driving element comprises a plurality of flat surfaces.

11. The assembly of claim 6, wherein the outer locking element and the inner locking element are generally cylindrical and are spaced apart so as to capture a wall of a spinal fixation element receiving body therebetween.

12. The assembly of claim 6, wherein the deformable spinal fixation element contacting element is configured, upon deformation, to form a cold weld with a spinal fixation element.

13. The assembly of claim 6, wherein the deformable spinal fixation element contacting element decreases in thickness from the first position to the second position.

14. The assembly of claim 6, wherein the outer locking element proximal mating element is a proximal plate having a central aperture.

15. The assembly of claim 14, wherein the inner locking element proximal mating element is a spindle rotatably mated to the proximal plate through the central aperture.

16. The assembly of claim 6, wherein the locking cap assembly is configured to avoid notching of the spinal fixation element by the deformable spinal fixation element contacting element upon tightening of the locking cap assembly to the spinal fixation element.

17. The assembly of claim 6, wherein at least a portion of the outer locking element is made of resilient material.

18. The assembly of claim 6, wherein the deformable spinal fixation element contacting element is in the form of a ring configured to provide secure four point locking of the spinal fixation element by the locking cap assembly.

19. The assembly of claim 18, wherein the outer locking element includes a resilient top portion configured to allow the inner locking element to move in a proximal and distal direction with respect to the outer locking element.

20. The assembly of claim 6, wherein the inner locking element contacts the spinal fixation element at two points and the outer locking element contact the spinal fixation element at two points.

21. The assembly of claim 6, further comprising a spinal fixation element, wherein the spinal fixation element is curved and the inner locking element contacts the spinal fixation element at two points and the outer locking element contact the spinal fixation element at two points.

22. A system for coupling a spinal fixation element to a patient's spine comprising:
  a spinal fixation element receiving body having a vertebral coupling element disposed on a first end of the body and a spinal fixation element receiving opening formed on a second end of the body, the body including an outer portion adapted to engage an outer locking element;
  a spinal fixation element receivable within the spinal fixation element receiving body;
  a locking cap assembly for locking the spinal fixation element to the spinal fixation element receiving body, the locking cap assembly including:
  an outer locking element having opposed proximal and distal ends and inner and outer surfaces, the outer locking element having a proximal mating element and an engagement element formed on the inner surface adjacent the distal end for engaging the outer portion of the spinal fixation element receiving body so as to close the spinal fixation element to the spinal fixation element receiving body upon tightening of the engagement element; and
  an inner locking element having proximal and distal ends, the inner locking element having a deformable spinal fixation element contacting ring disposed on its distal end and a proximal mating element on its proximal end rotatably mated to the outer locking element proximal mating element so that the inner locking element is rotatably mounted within the outer locking element;
  wherein tightening the spinal fixation locking cap assembly to the spinal fixation element receiving body to lock the spinal fixation element therein causes the deformable spinal fixation element contacting ring to contact the spinal fixation element and to deform the deformable spinal fixation element contacting ring to provide secure four point locking of the spinal fixation element within the spinal fixation element receiving body.

23. The system of claim 22, wherein the vertebral coupling element is a pedicle screw.

24. The system of claim 22, wherein the vertebral coupling element is a spinal hook.

25. The system of claim 22, wherein the engagement element comprises threads formed on the inner surface adjacent to the distal end.

26. The system of claim 25, wherein upon deformation of the deformable spinal fixation element contacting ring upon tightening of the outer locking element to the spinal fixation receiving element by turning, the inner locking element does not rotate with the turn of the outer locking element.

27. The system of claim 22, wherein a driving element is formed on the outer surface of the outer locking element.

28. The system of claim 27, wherein the driving element comprises a plurality of flat surfaces.

29. The system of claim 22, wherein the outer locking element and the inner locking element are generally cylindrical and are spaced apart so as to capture a wall of a spinal fixation element receiving body therebetween.

30. The system of claim 22, wherein the deformable spinal fixation element contacting ring extends from a first position at the distal end of the inner locking element that is proximal to the distal end of the outer locking element to a second position distal to the distal end of the outer locking element.

31. The system of claim 30, wherein the deformable spinal fixation element contacting ring decreases in thickness from the first position to the second position.

32. The system of claim 22, wherein the deformable spinal fixation element contacting ring is configured, upon deformation, to form a cold weld with the spinal fixation element.

33. The system of claim 22, wherein the outer locking element proximal mating element is a proximal plate having a central aperture.

34. The system of claim 33, wherein the inner locking element proximal mating element is a spindle rotatably mated to the proximal plate through the central aperture.

35. The system of claim 22, wherein the locking cap assembly is configured to avoid notching of the spinal fixation element by the deformable spinal fixation element contacting ring upon tightening of the locking cap assembly.

36. The system of claim 22, wherein the outer locking element is made of resilient material.

37. The system of claim 36, wherein only the top of the outer locking element is made of resilient material.

38. The system of claim 37, wherein the resilient top of the outer locking element allows the inner locking element to move in a proximal and distal direction with respect to the outer locking element.

39. The system of claim 22, wherein the inner locking element contacts the spinal fixation element at two points and the outer locking element contact the spinal fixation element at two points.

40. The system of claim 22, wherein the spinal fixation element is curved and the inner locking element contacts the spinal fixation element at two points and the outer locking element contact the spinal fixation element at two points.

* * * * *